(12) United States Patent  (10) Patent No.: US 6,554,828 B2
Schneiter  (45) Date of Patent: Apr. 29, 2003

(54) REUSABLE LAPAROSCOPIC SURGICAL INSTRUMENT

(75) Inventor: James A. Schneiter, Lake Forest, IL (US)

(73) Assignee: American Medical Products, Lake Forest, IL (US)

(*) Notice: Subject to any disclaimer, the term of this patent is extended or adjusted under 35 U.S.C. 154(b) by 0 days.

(21) Appl. No.: 09/851,037

(22) Filed: May 7, 2001

(65) Prior Publication Data

US 2002/0165538 A1 Nov. 7, 2002

(51) Int. Cl.$^7$ .............................................. A61B 18/18
(52) U.S. Cl. ........................................ 606/46; 600/562
(58) Field of Search ...................... 606/46, 190, 205, 606/207, 208, 174; 600/562–567

(56) References Cited

U.S. PATENT DOCUMENTS 5,074,311 A * 12/1991 Hasson ........................ 600/567
5,578,052 A * 11/1996 Koros et al. ................. 606/174
5,849,022 A * 12/1998 Sakashita et al. ........... 606/174
5,893,874 A *  4/1999 Bourque et al. ............. 606/170
6,228,083 B1 *  5/2001 Lands et al. ................. 600/207

OTHER PUBLICATIONS

Infection Control Today, "Instrumental Knowledge," Nancy Chu, M.S. and Martin Favero, Ph.D., Aug. 2, 2001.
Product Catalog, Endoscopic Instrumentation, Jarit The Instrument People, 1996.
Product Catalog, Codman Endoscopic Instruments, Codman & Shurtleff, Inc., distributed in or before the year 2000.
Product Catalog, Davol Precision Laparoscopic Instruments, Davol, Inc., distributed in or before the year 2000.
Product Catalog, Endoplus, Inc., Precision Endoscopic Instruments, distributed in or before the year 2000.
Photographs of Endoscopic Instruments sold prior to May, 2000.

* cited by examiner

Primary Examiner—Teresa Walberg
Assistant Examiner—Thor Campbell
(74) Attorney, Agent, or Firm—Brinks Hofer Gilson & Lione

(57) ABSTRACT

A surgical instrument having a handle and an elongated member. The elongated member has a proximal end and a distal end. The elongated member defines an interior passageway having a narrowed throat portion adjacent the distal end. The throat portion has a substantially smooth and cornerless continuous surface. A movable rod is located within the passageway of the elongated member and passes through the throat portion of the elongated member. A tool is connected to the operating rod and extends from the clevis portion of the elongated member.

27 Claims, 3 Drawing Sheets

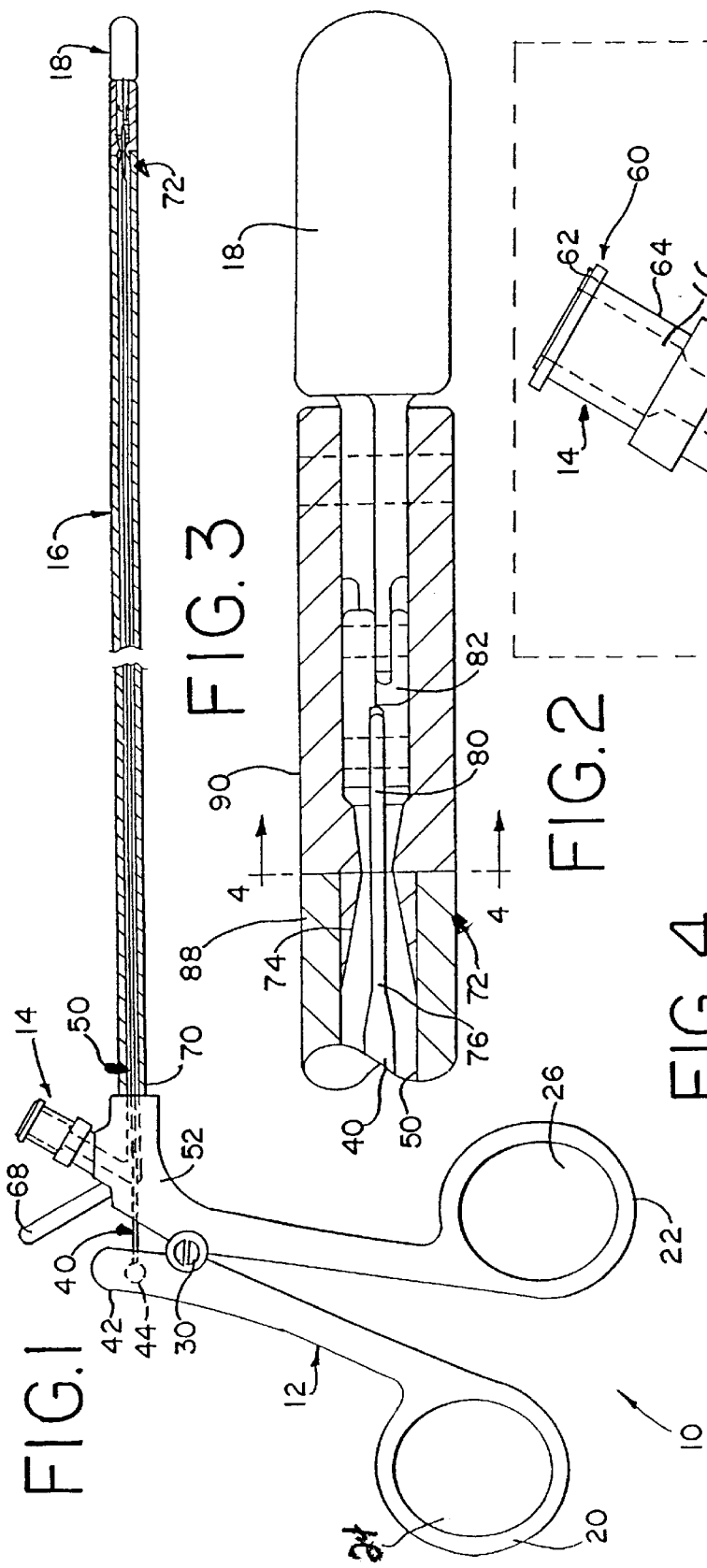
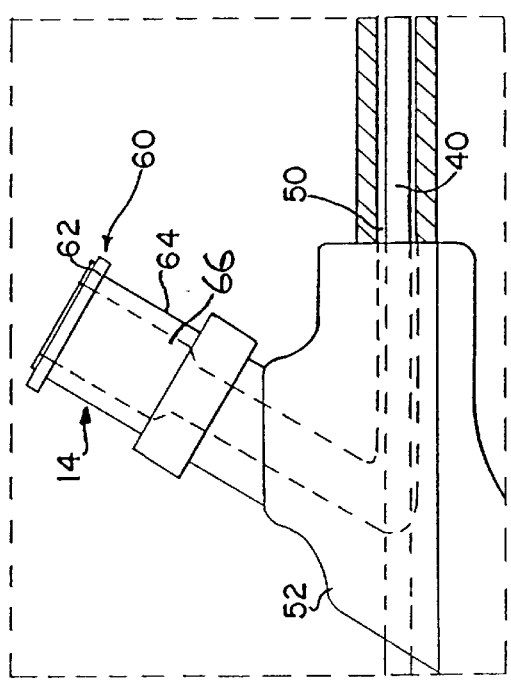
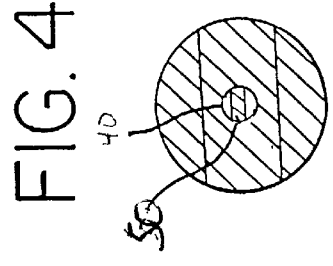

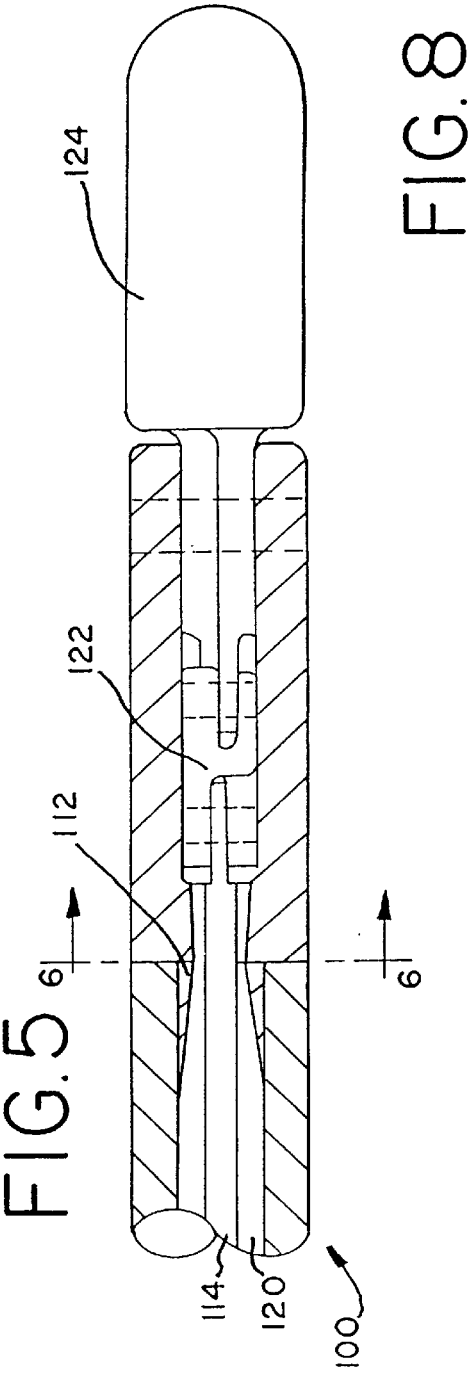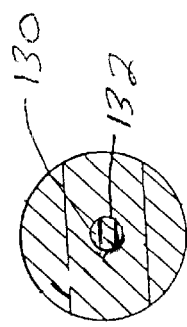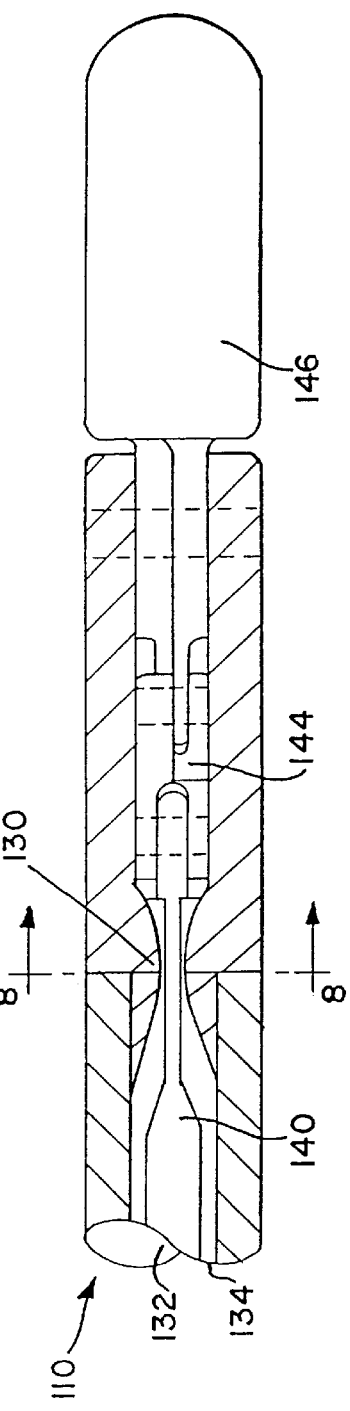

REUSABLE LAPAROSCOPIC SURGICAL INSTRUMENT

FIELD OF THE INVENTION

The present invention relates generally to the field of surgical instruments, e.g., laparoscopic instruments. More specifically, the present invention relates to a reusable hand held laparoscopic surgical instrument having improved flushing and cleaning/sterilization capabilities.

BACKGROUND OF THE INVENTION

The use of surgical instruments such as laparoscopic instruments during surgical procedures is known. One important consideration during such procedures is the protection of patients and healthcare personnel from disease transmission. Recently, the prevention of disease transmission has become even more important as emerging antibiotic resistant microorganisms have become more prevalent.

One significant problem with the use of surgical instruments is the removal of the bio-burden and/or microorganisms that build up inside the chamber of the instrument. During surgical procedures, the distal end of the lumen comes in contact with bio-burden such as blood, fat, protein, carbohydrates and starches. In particular, the positive pressure of the insufflated abdomen forces blood and other body fluids into the instrument and is difficult or impossible to remove. After the procedure, reusable instruments have to be cleaned and sterilized prior to use on the next patient. These instruments are extremely difficult to clean because of the long shaft and "dead spaces" within the lumen that trap bio-burden. Instruments that cannot be flushed and cleaned properly cannot be sterilized or disinfected with 100% certainty. Previous designs for such surgical instruments include a lumen that can promote the build-up of bioburden and microorganisms in the "dead spaces" and corners of the lumen, even when cleaned by highly skilled hospital personnel trained in instrument cleaning protocols.

One solution to this problem has been the development and use of single-use disposable instruments. While the use of a disposable instrument ensures the lack of bio-burden in the instrument, the cost is quite high because the instrument is disposed of after just one surgical procedure. In addition, disposable instruments are made of a lower quality material and lack the tactile feel, stability or strength of a reusable instrument. Another attempt at solving the problem has been the development of "modular" instruments that are disassembled and manually cleaned and scrubbed after each surgical procedure. Yet, these modular instruments are time-consuming and difficult to clean due to the "dead spaces" and the hard to clean corners inside the lumen.

A further approach to the removal of bio-burden and microorganisms in a laparoscopic instrument includes the use of a reusable instrument that has a flush port useful to clean the instrument. The flush port allows a cleaning solution to be flushed through the lumen of the instrument. However, this approach may not completely remove all of the bio-burden and microorganisms inside the lumen of the instrument. In particular, previous designs have included a lumen with corners that become partially occluded with a build-up of bio-burden over time.

Accordingly, there exists a need for a reusable surgical instrument with an internal chamber that allows for the efficient removal of bio-burden and microorganisms combined with maximum bacteria kill rates during steam sterilization.

SUMMARY OF THE INVENTION

The present invention is directed to a reusable surgical instrument with an improved lumen and "Clear Flush" chamber that eliminates corners and edges which collect bio-burden and microorganisms. The present invention also reduces the possibility of such a build-up within the lumen or passageway of the instrument by providing an improved flushing and cleaning/sterilization capability.

According to a first aspect of the invention, a surgical instrument having a handle and an elongated member is provided. The elongated member has a proximal end and a distal end. The elongated member defines an interior passageway having a narrowed throat portion adjacent the distal end. The throat portion has a substantially smooth and cornerless continuous surface. A movable rod is located within the passageway of the elongated member and passes through the throat portion of the elongated member. A tool is connected to the rod and extends from the distal end of the elongated member.

According to a second aspect of the invention, a medical device that is insertable into a body is provided. The medical device includes a handle and an elongated member. The elongated member is connected to the handle and includes a proximal end and a distal end. The elongated member includes an interior lumen having a narrowed throat portion adjacent the distal end. A movable rod is located within the lumen of the elongated member and passes through the throat portion of the lumen. The throat portion is at least partially and substantially spaced away from the rod in order to provide for a relatively unencumbered flow of fluid therethrough. A tool is connected to the rod and extends from the distal end of the lumen. A port is connected to the passageway of the lumen and is adapted to receive a cleaning solution for insertion through the passageway and out the distal end of the lumen.

According to a further aspect of the invention, a laparoscopic medical device that is insertable into a body is provided. The medical device includes a handle and an elongated member. The elongated member is connected to the handle. The elongated member has a proximal end and a distal end and includes an interior passageway having a narrowed throat portion adjacent the distal end. The throat portion has a substantially smooth and cornerless continuous surface. A movable rod is located within the passageway of the elongated member and passes through the throat portion of the elongated member. The throat portion is at least partially and substantially spaced away from the rod. A tool is connected to the operating rod and extends from the distal end of the elongated member. A port is connected to the passageway of the elongated member and is adapted to receive a cleaning solution for insertion through the passageway.

The present invention, together with attendant objects and advantages, will be best understood with reference to the detailed description below in connection with the attached drawings.

BRIEF DESCRIPTION OF THE DRAWINGS

FIG. 1 is an illustration of a laparoscopic instrument in accordance with a first embodiment of the present invention;

FIG. 2 is an enlarged view of a proximal end of the instrument of FIG. 1 illustrating the port;

FIG. 3 is an enlarged view of a distal end of the instrument of FIG. 1 illustrating the shaft, clevis and throat portions;

FIG. 4 is a cross-section taken along the lines 4—4 of FIG. 3;

FIG. 5 is an enlarged view of a distal end of the instrument according to another embodiment illustrating the shaft, clevis and throat portions;

FIG. 7 is an enlarged view of a distal end of the instrument according to a further embodiment illustrating the shaft, clevis and throat portions; and FIG. 8 is a cross-section of the embodiment of FIG. 7 taken along the lines 8—8.

DETAILED DESCRIPTION OF THE PREFERRED EMBODIMENTS

Figure 6:
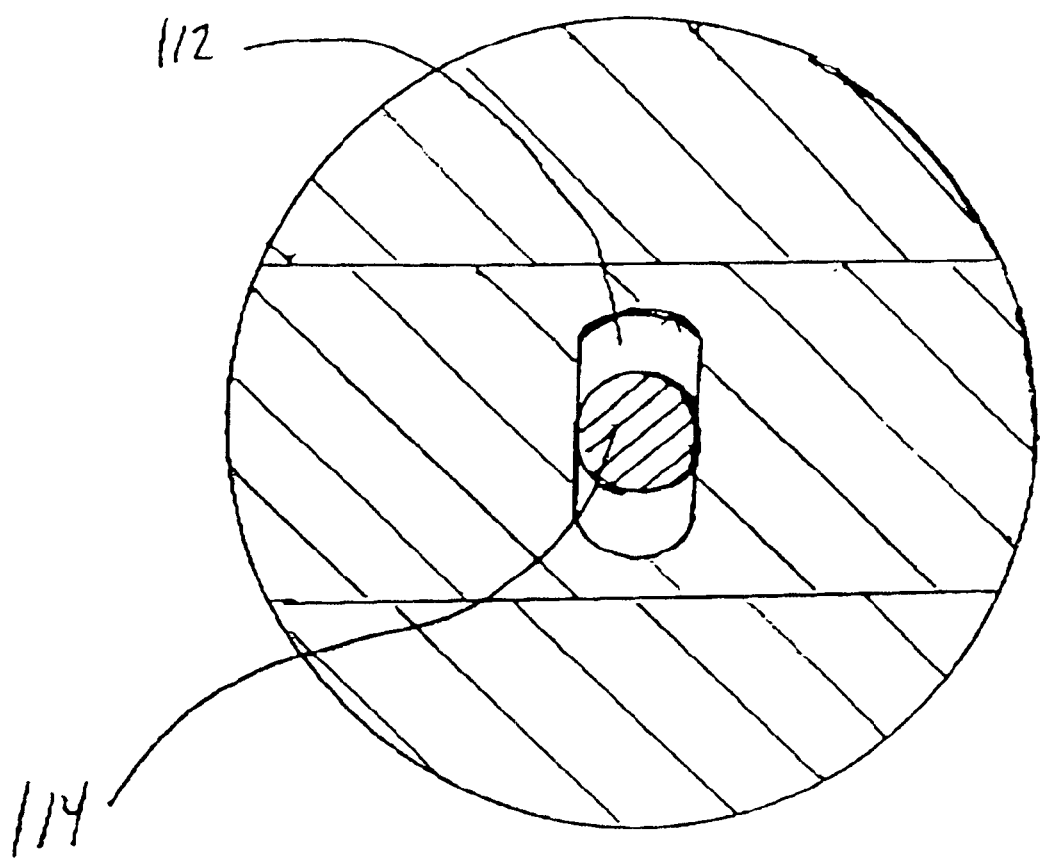
FIG. 6 is a cross-section of the embodiment of FIG. 5 taken along the lines 6—6.

The present invention is directed to an improved reusable surgical instrument that is more readily flushed, cleaned and sterilized than those commonly used. The cornerless interior lumen or passageway and the improved configuration of the throat portion thereof helps prevent the build-up of bio-burden and/or microorganisms. In addition, the present invention creates a pressurized laminar flow in the throat portion that is highly effective in removing bio-burden and microorganisms from the instrument during flushing and during cleaning/sterilization. The preferred embodiments are described generally in the context of laparoscopic surgical instruments. However, the principles of the invention apply equally well to other types of surgical instruments that have enclosed lumens and come in contact with bio-burden and microorganisms during surgical procedures.

FIG. 1 illustrates a laparoscopic surgical instrument 10 in accordance with a first embodiment of the present invention. The instrument 10 includes a handle 12, a port 14, an elongated member 16 and a tool 18. The handle 12 includes a front member 20 and a rear member 22. The front member 20 includes an opening 24 adapted to receive the thumb of a user. The rear member 22 includes an opening 26 adapted to receive the finger of a user. The front member 20 and the rear member 22 may be formed from conventional materials such as stainless steel or other metals such as nickel. Other materials such as carbon fiber or plastics such as Delrin™ may also be used. The handle 12 may also include an insulating coating such as nylon or Teflon™ to protect the user from electrical current.

A pin 30 interconnects the front member 20 and the rear member 22 and defines a pivot axis for the handle 12. The front member 20 is movable relative to the rear member 22. An operating rod 40 is connected to an upper portion 42 of the front member 20 and movable therewith. A ball 44 (shown in phantom lines) is welded to a distal end of the operating rod 40. The ball 44 is located within a pocket within the front member 20 in order to secure the operating rod 40 thereto. In operation, as a user pulls backwards on the front member 20, the operating rod 40 is pushed forward. As a user pushes forward on the front member 20, the operating rod 40 is pulled backward.

The rod 40 passes into a lumen or passageway 50 formed in an upper portion 52 of the rear member 22 of the handle 12. A port 14 is also connected to the upper portion 52 of the rear member 22 of the handle 12. As best seen in FIG. 2, the port 14 includes a luer connector 60 having an upper rim 62 that is secured to an associated syringe used to insert a cleaning solution into the passageway 50 formed in the upper portion 52 of the rear member 22 of the handle 12. The port 14 also includes a collar portion 64. The port 14 defines a port passageway 66 that connects to the passageway or lumen 50. Conventional cleaning solutions such as enzymatic detergents may be inserted through the passageway 66 of the port 14 into the passageway or lumen 50. Behind the port 14, an electrode post 68 for use in electrosurgery is located.

The elongated member 16 is connected to the upper portion 52 of the rear member 22 of the handle 12. The elongated member 16 includes an internal cavity that further defines the passageway or lumen 50 through which the operating rod 40 passes. The internal cavity of the elongated member 16 has a preferred diameter within the range of 2–15 mm with a diameter of 5 mm being generally preferred. However, as those of ordinary skill in the art will recognize, the diameter of the internal cavity diameter can be sized to suit the needs of a particular size instrument or tool. The elongated member 16 has a proximal end 70 and a distal end 72. In addition, the elongated member 16 preferably has a length generally with the range of 20–50 cm with 32 cm being generally preferred. With particular reference to FIGS. 3–4, the distal end 72 includes a throat portion 74. In this embodiment of the invention, the operating rod 40 includes an end portion 76 that tapers from a generally round shape to a flattened shape, i.e., a generally step-shaped configuration. This taper occurs generally adjacent the throat portion 74. The taper can be formed generally within the range of 10–75 degrees. Also, in the illustrated embodiment, the throat portion 74 is formed from a inverted generally v-shaped wall. With reference to FIG. 4, the end portion 76 passes through a generally round portion (in cross-section) of the passageway 50 in the area of the throat portion 74.

The present invention is characterized by a throat portion 74 that is cornerless which thereby helps prevent the build-up of bio-burden and microorganisms. The present invention also creates a pressurized laminar flow, i.e., a Venturi-type chamber, in the throat portion 74 that is highly effective in removing bio-burden and microorganisms from the instrument during flushing and during cleaning/sterilization. In addition, the throat portion 74 is substantially spaced away from the operating rod 40 in order to allow for cleaning solutions and/or steam during sterilization to readily pass through the passageway 50 to ensure total bacteria kill.

The end portion 76 of the operating rod 40 passes through the throat portion 74 and connects to the tool 18. More specifically, the end portion 80 of the tool 18 is connected to the hinge 82. In the preferred embodiment, the elongated member 16 includes a shaft portion 88 and a clevis portion 90 formed from two separate pieces. As recognized by those of ordinary skill in the art, the tool 18 can take a wide variety of forms such as a grasping forcep, a curved dissecting forcep, a curved Maryland dissector, a Babcock grasping forcep and other related tools.

As will also be recognized by those of ordinary skill in the art, the shaft portion 88 and the clevis portion 90 are electronically welded together and then finished. The operating rod 40, the shaft portion 88 and the clevis portion 90 can be formed from conventional metals with stainless steel being the preferred material. In the preferred embodiment, the operating rod 40 and the passageway 50 are superfinished to meet an ANSI B46 standard of 2–8 microinches of roughness. The operating rod 40 and passageway can then be plated with materials such as gold, chrome or nickel with gold being the most preferred material. The use of superfinishing and a plating material creates a very smooth surface to which it is more difficult for bio-burden to attach. In addition, such a surface is more readily cleaned.

FIGS. 5–8 illustrate two additional embodiments 100 & 110 of the present invention that operate in essentially the same way as does the embodiment of FIGS. 1–4. However, with reference to FIGS. 5 & 6, the throat portion 112 is configured to have an oblong shape (in cross-section) as best illustrated in FIG. 6. This shape is particularly useful with an operating rod having a generally round shape in the area of the throat portion 112. Again, the embodiment of FIGS. 5 & 6 includes the elements of a passageway 120 and a tool 124 having a hinge 122.

Another embodiment is illustrated in FIGS. 7 & 8. The embodiment of FIGS. 7 & 8 includes a curved throat portion 130. The operating rod 132 passes through the passageway 134 and tapers 140 in the area of the curved throat portion 130. A cross-section of this embodiment is illustrated in FIG. 8. The shape of the operating rod 132 is generally the same as the operating rod 40 illustrated in FIGS. 1–4. Again, the embodiment of FIGS. 7 & 8 includes the tool 146 having a hinge 144.

Again, with respect to embodiments of FIGS. 5–8, the throat portions 112 & 130 are essentially cornerless to prevent the collection of bio-burden. In addition, the throat portions 112 & 130 create a pressurized laminar flow of fluid therethrough when cleaned. Also, the spacing between the throat portions 112 & 130 and the operating rods 114 & 132 allows for increased effectiveness of the steam during the sterilization processes.

The embodiments described above and shown herein are illustrative and not restrictive. The scope of the invention is indicated by the claims rather than by the foregoing description and attached drawings. The invention may be embodied in other specific forms without departing from the spirit of the invention. For example, the type and size of the instrument may be designed in a manner other than as specifically illustrated in the figures. Accordingly, these and any other changes which come within the scope of the claims are intended to be embraced herein.

I claim:

1. A flushable surgical instrument comprising:
  a) a handle;
  b) an elongated member connected to a handle, the elongated member having a proximal end and a distal end, the elongated member defining an interior passageway having a narrowed throat portion adjacent the distal end, the throat portion having a substantially smooth and cornerless continuous surface;
  c) a movable rod located within the passageway of the elongated member and passing through the throat portion of the elongated member, the movable rod and the interior passageway being superfinished, the throat portion and the interior passageway being at least partially spaced away from the rod in order to provide for a relatively unencumbered flow of a pressurized cleaning fluid therethrough;
  d) a tool connected to the rod and extending from the distal end of the elongated member.

2. The surgical instrument of claim 1 wherein the elongated member is formed from at least two separate pieces, a shaft portion and a clevis portion.

3. The surgical instrument of claim 2 wherein the rod has a substantially round cross-section.

4. The surgical instrument of claim 3 wherein the throat portion of the elongated member has a generally oblong cross-section.

5. The surgical instrument of claim 4 wherein the throat portion of the elongated member has a generally inverted v-shaped wall.

6. The surgical instrument of claim 2 wherein the rod includes a flattened portion adjacent the distal end of the elongated member.

7. The surgical instrument of claim 6 wherein the throat portion of the elongated member has a generally round cross-section.

8. The surgical instrument of claim 7 wherein the throat portion of the elongated member has a generally inverted v-shaped wall.

9. The surgical instrument of claim 8 wherein the flattened portion of the rod extends from the shaft portion into the clevis portion.

10. A flushable medical device that is insertable into a body, comprising:
  a) a handle;
  b) an elongated member connected to the handle, the shaft having a proximal end and a distal end, the elongated member defining a substantially cornerless interior passageway having a throat portion adjacent the distal end;
  c) a movable rod located within the passageway of the elongated member and passing through the throat portion of the elongated member, the throat portion and the interior passageway being at least partially spaced away from the rod in order to provide for a relatively unencumbered flow of a pressurized cleaning fluid therethrough;
  d) a tool connected to the rod and extending from the distal end of the elongated member; and
  e) a port connected to the passageway of the elongated member and adapted to receive a cleaning solution for pressurized insertion through the passageway and out the distal end of the elongated member.

11. The medical device of claim 10 wherein the elongated member is formed from at least two separate pieces, a shaft portion and a clevis portion.

12. The medical device of claim 11 wherein the rod has a substantially round cross-section.

13. The medical device of claim 12 wherein the throat portion of the elongated member has a generally oblong cross-section.

14. The medical device of claim 13 wherein the throat portion of the elongated member has a generally inverted v-shaped wall.

15. The medical device of claim 10 wherein the rod includes a flattened portion adjacent the distal end of the elongated member.

16. The medical device of claim 15 wherein the throat portion of the elongated member has a generally round cross-section.

17. The medical device of claim 16 wherein the throat portion of the rod has a generally stepped configuration.

18. The medical device of claim 17 wherein the flattened portion of the rod extends from the shaft portion into the clevis portion.

19. A flushable laparoscopic medical device that is insertable into a body, comprising:
  a) a handle;
  b) an elongated member connected to the handle, the elongated member having a proximal end and a distal end, the elongated member defining an interior passageway having a narrowed throat portion adjacent the distal end, the throat portion having a smooth and cornerless continuous surface;
  c) a movable rod located within the passageway of the elongated member and passing through the throat portion of the elongated member, the throat portion and the interior passageway being at least partially spaced away from the rod;

d) a tool connected to the operating rod and extending from the elongated member; and e) a port connected to the passageway of the elongated member and adapted to receive a cleaning solution for pressurized insertion through the passageway.

20. The medical device of claim 19 wherein the shaft is formed from at least two separate pieces, a shaft portion and a clevis portion.

21. The medical device of claim 20 wherein the rod has a substantially round cross-section.

22. The medical device of claim 21 wherein the throat portion of the elongated member has a generally oblong cross-section.

23. The medical device of claim 22 wherein the throat portion of the elongated member has a generally inverted v-shaped wall.

24. The medical device of claim 19 wherein the rod includes a flattened portion adjacent the distal end of the elongated member.

25. The medical device of claim 24 wherein the throat portion of the elongated member has a generally round cross-section.

26. The medical device of claim 25 wherein the throat portion of the elongated member has a generally inverted v-shaped wall.

27. The medical device of claim 26 wherein the flattened portion of the rod extends from the shaft portion into the clevis portion.

* * * * *